United States Patent
Lappalainen

(10) Patent No.: US 8,580,572 B2
(45) Date of Patent: Nov. 12, 2013

(54) LATERAL FLOW ASSAY TEST STRIP AND METHOD OF MAKING THE SAME

(75) Inventor: Timo Lappalainen, Jyväskylä (FI)

(73) Assignee: Teknologian Tutkimuskeskus, Vtt (FI)

( * ) Notice: Subject to any disclaimer, the term of this patent is extended or adjusted under 35 U.S.C. 154(b) by 0 days.

(21) Appl. No.: 13/318,761

(22) PCT Filed: May 3, 2010

(86) PCT No.: PCT/FI2010/050358
§ 371 (c)(1),
(2), (4) Date: Mar. 16, 2012

(87) PCT Pub. No.: WO2010/128205
PCT Pub. Date: Nov. 11, 2010

(65) Prior Publication Data
US 2012/0164028 A1    Jun. 28, 2012

(30) Foreign Application Priority Data

May 4, 2009 (FI) ..................... 20095503

(51) Int. Cl.
*G01N 33/48* (2006.01)
(52) U.S. Cl.
USPC .......... 436/165; 422/68.1; 422/400; 422/420; 422/421; 422/430; 422/426; 422/425
(58) Field of Classification Search
USPC ........ 422/68.1, 400, 420, 421, 425, 426, 430; 436/164, 165
See application file for complete search history.

(56) References Cited

U.S. PATENT DOCUMENTS

| | | | |
|---|---|---|---|
| 4,298,688 A | 11/1981 | Kallies | |
| 5,200,317 A | 4/1993 | Georgevich | |
| 5,916,521 A * | 6/1999 | Bunce et al. | 422/422 |
| 2003/0045001 A1 | 3/2003 | Burgess et al. | |
| 2003/0211634 A1 | 11/2003 | Jerome et al. | |

FOREIGN PATENT DOCUMENTS

| | | |
|---|---|---|
| AU | 734603 | 4/1999 |
| EP | 0 381 173 A1 | 8/1990 |
| EP | 1 936 376 A2 | 6/2008 |
| WO | WO 96/35123 | 11/1996 |
| WO | WO 2007/149042 A1 | 12/2007 |
| WO | WO 2008/018073 A1 | 2/2008 |
| WO | WO 2008/030546 A2 | 3/2008 |

* cited by examiner

*Primary Examiner* — Lyle Alexander
(74) *Attorney, Agent, or Firm* — Patterson Thuente Pedersen, P.A.

(57) ABSTRACT

The invention relates to a lateral flow assay test strip and a method for making the same. The strip comprises, in the flow direction, a selectively activated membrane for a test reaction and an absorption pad, which are both made of paper and may comprise an integral paper strip. The absorption pad has the paper strip embossed and/or folded to increase the strip's absorption capacity. The folded pad may have an accordion-like configuration, the strip running to-and-from, or it may have the strip rolled and then flattened to a stack of layers.

22 Claims, 2 Drawing Sheets

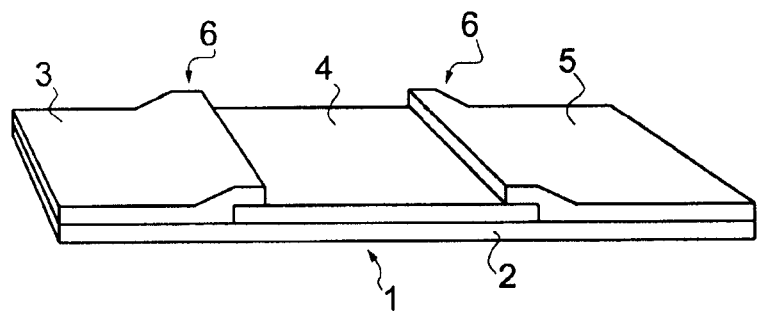
Fig. 1
Prior Art
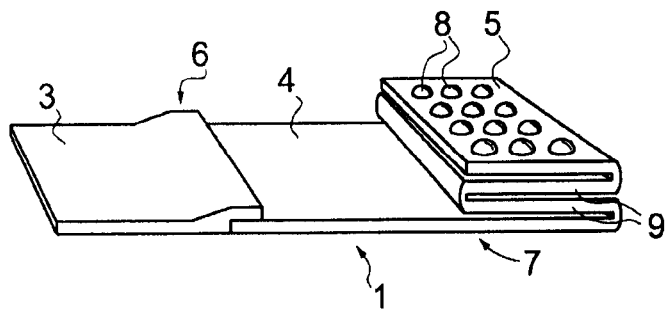
Fig. 2
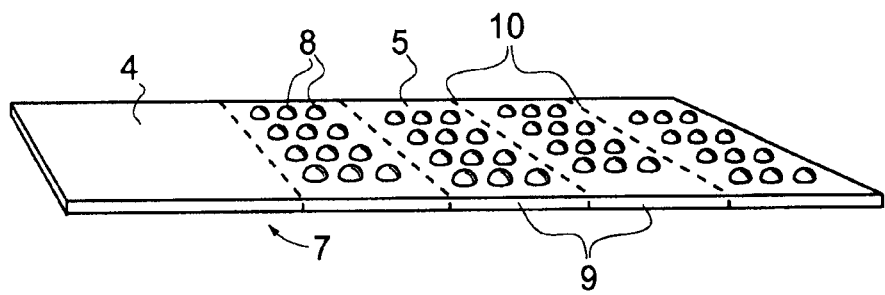
Fig. 3
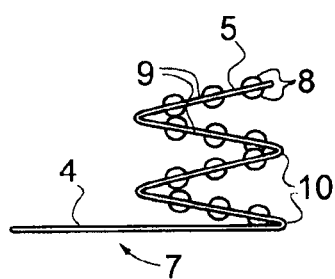 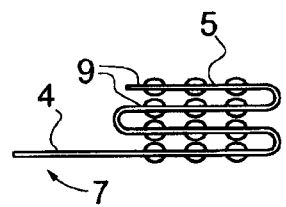
Fig. 4a  Fig. 4b

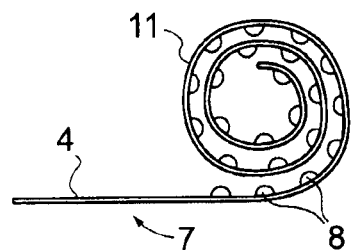
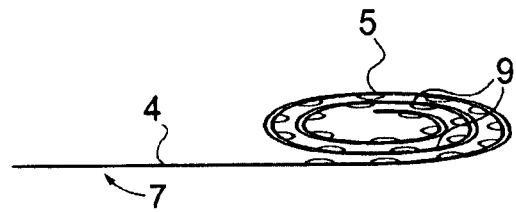
Fig. 5a  Fig. 5b
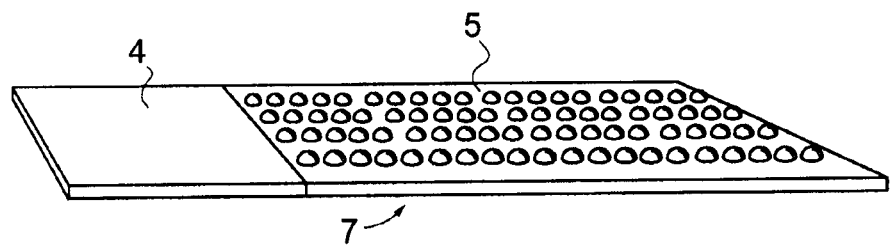
Fig. 6
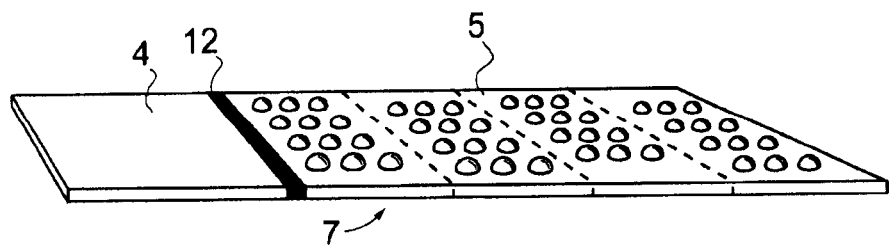
Fig. 7

LATERAL FLOW ASSAY TEST STRIP AND METHOD OF MAKING THE SAME

PRIORITY CLAIM

The present application is a National Phase entry of PCT Application No. PCT/FI2010/050358, filed May 3, 2010, which claims priority from Finnish Application Number 20095503, filed May 4, 2009, the disclosures of which are hereby incorporated by reference herein in their entirety.

FIELD OF THE INVENTION

The invention concerns a lateral flow assay test strip comprising, in the flow direction, a selectively activated membrane for a test reaction and an absorption pad, as well as a method of making such a test strip.

BACKGROUND OF THE INVENTION

Assay tests are used in vitro medical diagnostics to detect biomolecules such as enzymes or antibodies in liquid samples derived from patients. Testing means, usually in the form of a test strip, comprise a reagent chosen to be selectively reactive with the biomolecule to be detected or a derivate thereof, yielding a reaction product, the presence of which can be seen visually or shown by detection means.

A typical prior art assay test strip is described in the publication WO 2008/018073. A non-absorbing backing laminate is arranged to support a sample pad, a reaction membrane, and an absorption pad, there being a controlled overlap between the sample pad and the reaction membrane, and between the reaction membrane and the absorption pad, respectively. A non-absorbing top laminate can be placed to partially cover said three successive parts of the strip. In use of the strip the liquid sample to be tested is supplied onto the free surface of the sample pad. The liquid phase, including the analyte, is drawn to the reaction membrane comprising one or more reagents selectively reacting with the analyte in a reaction or a series of reactions. A lateral liquid flow through the strip is generated by capillary force from the absorption pad, the latter thus accumulating liquid which has passed the reaction membrane. As materials for the strip the reference cites glass fiber or filter paper for the sample pad, nitrocellulose or a nylon membrane for the reaction membrane, and cellulose or filter paper for the absorption pad.

The usual material for the reaction membrane in commercial test strips is nitrocellulose. However, a problem with nitrocellulose is its mechanical weakness. Furthermore, a separate absorption pad of different material, usually cellulose, has to be joined with the reaction membrane to form the distal accumulator end of the test strip. In the manufacture there must be a carefully controlled overlap between the two parts glued together to ensure that the flow dynamics is uniform in each strip produced, and the absorption pad must be bulky enough to allow variable sample sizes as well as washing of the flow path in the strip or sample lines upstream of it as necessary. The use of two materials as well as the two-part structure with a glue joint between the parts thus complicate the manufacture of the strip.

The problem could be avoided by use of the same material for the reaction membrane and the absorption pad. As regards nitrocellulose the material is too brittle for that and could not be adapted to work as an absorbent. A commercial test strip, in which the membrane and the absorption pad are both of glass fibre, is available, but the lateral flow speed in such a strip is too high and causes a sensitivity problem.

SUMMARY OF THE INVENTION

A solution according to the present invention is based on use of paper for the selectively activated reaction membrane in the test strip. The same paper material then constitutes the absorption pad also. Paper sheet material as such would have insufficient absorption capacity if used as a single layer, but according to the invention the absorption pad has the paper embossed and/or folded to increase the pad's absorption capacity.

Features and advantages of the use of bioactivable paper for the reaction membrane and the absorption pad are superior mechanical strength as compared to nitrocellulose and flexibility allowing the embossing and folding operations as well as modification of absorbency. Paper has a low price and when disposed, as opposed to nitrocellulose, it is biodegradable.

In an embodiment of the invention, the reaction membrane and absorption pad comprise an integral paper strip. The advantage is that there is no overlapping and joining of said two parts in the manner described e.g. in WO 2008/018073. The risk of inaccurate or variable overlap and non-uniformity of the strips as produced, which are major handicaps of the prior art, are wholly avoided, and the manufacture is considerably simplified.

According to an embodiment of the invention the absorption pad has the paper strip folded transversally to comprise a plurality of adjacent paper layers. Thus the folded paper strip may have an accordion-like configuration comprising a stack of paper layers running to-and-from. Alternatively the paper strip can be rolled and then flattened to turn the roll plies into a stack of adjacent paper layers.

In embodiments, the embossing made to the paper strip material may be protrusions forming a regular pattern over the absorption pad. Embossing is preferably combined with folding of the paper strip, the protrusions creating voids, i.e. empty air space between adjacent paper layers, which increase the absorption capacity of the pad. In this case the protrusions may be arranged between the folding lines, and both sides of the paper strip can be embossed so as to have protrusions between each pair of paper layers in the to-and-from configuration.

In embodiments, in order to increase its absorption capacity the paper of the absorption pad may be treated chemically, e.g. with a surfactant such as polyvinyl alcohol or polyoxy alcohol. It is also possible to have a superabsorbent, for instance cellulose wadding, located between the paper layers of the absorption pad to add to the absorption capacity.

In embodiments, the absorption pad the adjacent layers of the folded paper strip may be bonded to each other locally by gluing or by mechanical means, such as staples.

To receive the liquid sample the test strip according to embodiments of the invention, may comprise a non-activated sample inlet zone of fibrous material located as first in the flow direction.

The test strip according to embodiments of the invention is useful for immunoassay, enzyme or nucleic acid based assays and in assays based on a chemical reaction.

The method of making a lateral flow assay test strip according to embodiments of the invention having both the selectively activated membrane for a test reaction and the absorption pad made from a paper strip material, and the paper strip of the absorption pad may be embossed and/or folded to increase the strip's absorption capacity. Preferably the selectively activated reaction membrane and the absorption pad are made from an integral paper strip without cutting or breaking it into two.

DESCRIPTION OF THE DRAWINGS

The invention is now described in more detail with reference to the enclosed drawings, in which FIG. 1 shows a test strip according to the prior art, including a sample pad, a reaction membrane and an absorption pad of three different materials, FIG. 2 shows a test strip with a folded absorption pad according to an embodiment of the invention, FIG. 3 shows an integral paper strip forming the reaction membrane and the absorption pad of a test strip according to an embodiment of the invention, FIGS. 4a and 4b are a schematic depiction of folding of the absorption pad seen in FIG. 3, FIGS. 5a and 5b are a schematic depiction of folding an absorption pad by rolling and flattening of the same as a further embodiment of the invention, FIG. 6 shows in the manner of FIG. 3 an alternative paper strip for use in the invention, and FIG. 7 shows a further alternative, in which a reaction membrane of paper and an embossed absorption pad of paper have been glued together to form a paper strip for use in the invention.

DETAILED DESCRIPTION

The prior art lateral flow assay test strip 1 of FIG. 1 comprises a non-absorbing backing laminate 2 supporting a sample pad 3, a reaction membrane 4 and an absorption pad 5. The sample pad 3, the reaction membrane 4, and the absorption pad 5 are separate parts, joined by controlled overlaps 6 and gluings between the sample pad 3 and the reaction membrane 4, and between the reaction membrane 4 and the absorption pad 5, respectively. A non-absorbing top laminate (not shown) may be placed to partially cover said three successive parts 3, 4 and 5 of the strip 1. The sample pad 3 can be made of glass fiber or filter paper, the reaction membrane 4 is made of nitrocellulose, and the absorption pad 5 is made of cellulose or filter paper.

The test strip 1 shown in FIG. 1 is used by bringing a liquid sample to be tested onto the free upper surface of the sample pad 3, uncovered by a top laminate (if any). The liquid is drawn to the reaction membrane 4 activated by provision of at least one reagent selectively reacting with an analyte contained in the sample, such as an enzyme or an antibody. The reaction may be seen visually or verified, qualitatively or quantitatively, by a suitable detector known to a skilled person. The lateral liquid flow from the sample pad 3 through the reaction membrane 4 to the absorption pad 5 is generated by capillary force from the absorption pad 5, the latter thus displacing and accumulating liquid which has served for the reaction in the membrane 4.

An improved lateral flow assay test strip 1 according to the invention is depicted in FIG. 2. In conformity with the prior art test strip of FIG. 1, the test strip 1 of the invention comprises as functional parts a sample pad 3, a reaction membrane 4 and an absorption pad 5. There is also an overlap 6 between the sample pad 3 and the reaction membrane 4, which can be made of different materials, e.g. different grades of paper. As distinguished from the prior art test strip of FIG. 1, however, the reaction membrane 4 and the absorption pad 5 form an integral part made of a single paper strip 7. The reaction membrane part 4 of the paper strip 7 has been activated by inclusion of the one or more reagents for selective reaction(s) with the analyte to be detected from the sample, and the absorption pad part 5 of the paper strip 7 has been provided by embossing 8 and then folded transversally to form multiple paper layers 9 with an enhanced absorption capacity. Suitable wood raw materials for the paper strip 7 are eucalyptus and acacia. A backing laminate 2 such as seen in FIG. 1 or other water resistant substrate (not shown in FIG. 2) is preferably attached to the bottom of the strip 7 to hold the liquid flow within the strip.

FIG. 3 shows the paper strip 7 included as part of the test strip 1 according to the invention, before folding of the absorption pad 5. FIGS. 4a and 4b are a schematic depiction of the folding operation. The first part of the paper strip 7, about a quarter to half of its length, forming the reaction membrane 4 has smooth surfaces without marked protrusions, whereas the second part, which will form the absorption pad 5, has been divided into equal sections 9 by transversal folding lines 10, perpendicular to the length of the strip, and each part has embossings in the form of protruding knobs 8 as a regular rank-and-file pattern. Preferably both sides of the absorption pad part of the paper strip 7 are embossed in like manner. When the embossed part of the paper strip 7 is folded and the sections 9 defined by the folding lines 10 are pressed together as shown in FIGS. 4a and 4b, to form a stack of paper layers 9 running back and forth, the embossings 8 leave empty air space between adjacent paper layers and increase the total thickness of the absorption pad 5. The capacity of the absorption pad 5 to hold liquid is thus considerably increased, due to both the embossings and the subsequent folding operations.

It is to be noted that mere embossing of the paper strip, or mere folding of the same, markedly increase the strip's liquid holding capacity. Such strips are included in the scope of the invention as claimed. However, the full effect of increased absorbancy is achieved by the preferred combination of embossing and folding as described herein. In order to further increase the absorption capacity of the absorption pad (5) the paper forming the same can be treated chemically, or a superabsorbent can be located between the paper layers (9) of the stack forming the absorption pad (5).

FIGS. 5a and 5b show an alternative way of turning an embossed part of a paper strip 7 to a multilayer absorption pad 5. In this case the part of the paper strip 7 with embossing 8 is bent to a roll 11, which is then flattened by pressing to turn the roll plies into the superimposed paper layers 9 of the absorption pad 5. Folding lines 10 in the embossed part of the strip 7 may not be necessary. Another benefit is that only one side of the paper strip 7 needs to have embossing 8 to create the desired air space between the paper layers, although embossing on both sides of course works as well.

FIG. 6 shows an integral paper strip 7 for use in the test strip 1 according to the invention, as an alternative to the one depicted in FIG. 3. The second part 5 of the strip 7 has no folding lines 10 or other separations but only a regular pattern of embossings 8 covering said part entirely. This embodiment is particularly suitable for folding the strip by rolling and flattening as depicted in FIGS. 5a and 5b.

FIG. 7 shows a further alternative to the paper strip 7 of FIG. 3. In this case the activated reaction membrane 4 and the embossed absorption pad 5 are separate pieces of paper strip material, which have been glued together without overlapping to form a paper strip 7 for use in the invention, e.g. the test strip 1 according to FIG. 2. The circumstance of the gluing 12 being impervious to liquid flow may be overcome by a minor overlap between the folded absorption pad 5 and the non-embossed membrane 4 allowing an upright flow of liquid past the glue seam. The seam 12 is thus does not mark the borderline between the reaction membrane 4 and the folded absorption pad 5, but is rather located at the bottom of the latter.

A skilled person will understand that the embodiments as described above are only for illustration of the invention and not limiting the same, the metes and bounds of the invention being as defined in the appended claims.

The invention claimed is:

1. A lateral flow assay test strip comprising, in the flow direction, a selectively activated membrane having one or more reagents for a test reaction and an absorption pad, wherein the selectively activated membrane and the absorption pad are made from the same continuous paper strip, at least a portion of the absorption pad having an embossing comprising a plurality of protruding knobs on at least one side and a folded or a rolled configuration to provide a plurality of adjacent paper layers, whereby the embossing and the folded or rolled configuration provides an increased absorption capacity of the test strip.

2. A test strip according to claim 1, wherein the folded configuration of the absorption pad has the paper strip folded transversally to comprise a plurality of adjacent paper layers.

3. A test strip according to claim 2, wherein the folded configuration of the absorption pad has a to-and-from configuration.

4. A test strip according to claim 2, wherein a superabsorbent is located between the plurality of adjacent paper layers of the absorption pad.

5. A test strip according to claim 1, wherein the absorption pad has the folded configuration that is further pressed together to provide a stack of the plurality of adjacent paper layers.

6. A test strip according to claim 1, wherein in the absorption pad has the rolled configuration that is further flattened to provide a flattened roll configuration to provide a stack of the plurality of adjacent paper layers.

7. A test strip according to claim 6, wherein the test strip comprises a non-activated sample intake zone of fibrous material positioned before the selectively active membrane and the absorption pad in the flow direction.

8. A test strip according to claim 6, wherein a superabsorbent is located between the plurality of adjacent paper layers of the absorption pad.

9. A test strip according to claim 1, wherein in the absorption pad the adjacent layers of the folded paper strip are bonded to each other locally by one of gluing and by mechanical connection.

10. A test strip according to claim 9, wherein the test strip comprises a non-activated sample intake zone of fibrous material positioned before the selectively active membrane and the absorption pad in the flow direction.

11. A test strip according to claim 1, wherein the test strip comprises a non-activated sample intake zone of fibrous material positioned before the selectively active membrane and the absorption pad in the flow direction.

12. A test strip according to claim 11, wherein the paper of the absorption pad has been treated chemically to increase its absorption capacity.

13. A test strip according to claim 1, wherein the paper of the absorption pad has been treated chemically to increase its absorption capacity.

14. A test strip according to claim 1, wherein a superabsorbent is located between the plurality of adjacent paper layers of the absorption pad.

15. A test strip to claim 1, further comprising a plurality of voids filled with air located between at least a portion of the plurality of adjacent paper layers.

16. A test strip to claim 1, wherein the plurality of protruding knobs has a patterned configuration on the absorption pad.

17. A test strip to claim 1, wherein the embossing is on both sides of the absorption pad.

18. A method of making a lateral flow assay test strip comprising:
    forming a selectively activated membrane having one or more reagents for a test reaction and an absorption pad from the same strip of paper material;
    embossing at least a portion of the absorption pad, the embossed portion comprising a plurality of protruding knobs; and
    folding or rolling the absorption pad to provide a folded or rolled configuration comprising a plurality of adjacent paper layers;
    wherein the embossed portion of the absorption pad and the folded or rolled configuration providing the plurality of adjacent paper layers increases an absorption capacity of the test strip.

19. A method according to claim 18, wherein said membrane and absorption pad are made from an integral paper strip without cutting or breaking it into two.

20. A method according to claim 18, wherein the step of folding or rolling the absorption pad to provide a plurality of adjacent paper layers further provides a plurality of air-filled voids proximately located between at least a portion of the plurality of adjacent paper layers.

21. A lateral flow assay test strip comprising:
    a sample pad at a first end and at an opposing second end a continuous strip of paper material, the continuous strip of paper material having an activated portion having one or more reagents for a test reaction proximate to the sample pad and an absorption pad portion opposite from the sample pad, the absorption pad portion having an embossing comprising a plurality of protrusions on at least one side and a folded or a rolled configuration to provide a plurality of adjacent paper layers, whereby the embossing and the folded or rolled configuration provides an increased absorption capacity of the test strip.

22. The test strip of claim 21 wherein the strip of paper at the absorption pad portion has layers and has a super absorbent located therebetween.

* * * * *